(12) United States Patent
Speckbacher et al.

(10) Patent No.: US 7,452,385 B2
(45) Date of Patent: Nov. 18, 2008

(54) NAPHTHALENE DERIVATIVES AND COLORANTS FOR KERATIN FIBERS CONTAINING THESE COMPOUNDS

(75) Inventors: Markus Speckbacher, Mschaffenburg (DE); Hans-Juergen Braun, Ueberstorf (DE)

(73) Assignee: Wella AG, Darmstadt (DE)

( * ) Notice: Subject to any disclaimer, the term of this patent is extended or adjusted under 35 U.S.C. 154(b) by 202 days.

(21) Appl. No.: 10/585,033

(22) PCT Filed: Oct. 20, 2004

(86) PCT No.: PCT/EP2004/011853

§ 371 (c)(1),
(2), (4) Date: Jun. 29, 2006

(87) PCT Pub. No.: WO2005/075481

PCT Pub. Date: Aug. 18, 2005

(65) Prior Publication Data
US 2007/0157398 A1    Jul. 12, 2007

(30) Foreign Application Priority Data
Feb. 7, 2004    (DE) .................. 10 2004 006 143

(51) Int. Cl.
A61Q 5/10    (2006.01)
C09B 3/70    (2006.01)
(52) U.S. Cl. .................. 8/405; 8/406; 8/454; 8/570; 8/572; 8/607; 552/284
(58) Field of Classification Search .................. 8/405, 8/406, 454, 570, 572, 607; 552/284
See application file for complete search history.

(56) References Cited
U.S. PATENT DOCUMENTS
5,886,183 A    3/1999    Langhals et al.

FOREIGN PATENT DOCUMENTS

| EP | 0 769 532 | 4/1997 |
|---|---|---|
| FR | 1 075 110 | 10/1954 |
| GB | 1337 990 | 11/1973 |
| JP | 39 027124 | 11/1964 |
| JP | 48 099465 | 12/1973 |
| JP | 9-319110 | 12/1997 |
| JP | 2004 093791 | 3/2004 |
| WO | 00/40657 | 7/2000 |

OTHER PUBLICATIONS
STIC Search Report dated Mar. 4, 2008.*
(Continued)

*Primary Examiner*—Eisa B Elhilo
(74) *Attorney, Agent, or Firm*—Michael J. Striker

(57) ABSTRACT

The agent for coloring keratin fibers, especially human hair, contains at least one common cosmetic additive; an oxidant, such as hydrogen peroxide; and at least one naphthalene derivative of formula (I):

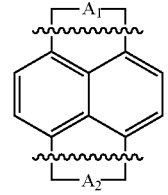

(I)

wherein $A_1$ and $A_2$ are different from each other and, independently of each other, each denote a partial structure of formula (II), (IIIa), (IIIb), (IV), (V), or (VI):

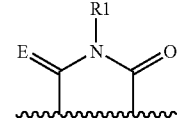

(II)

(IIIa)

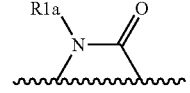

(IIIb)

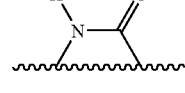

(IV)

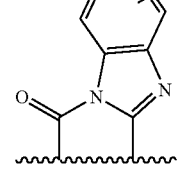

(V)

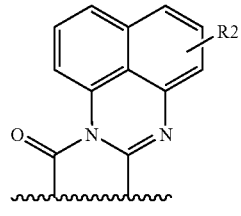

(VI)

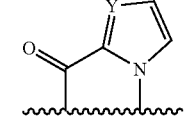

E is O or S; Y is N or a quaternary nitrogen atom substituted with a $C_1$-$C_6$-alkyl group, a $C_2$-$C_4$-hydroxyalkyl group, or a $C_4$-$C_6$-polyhydroxyalkyl group. New naphthalene derivatives are also described.

9 Claims, No Drawings

OTHER PUBLICATIONS

S.S Dalvi et al: "New Dyes From . . . " Indian Journal of Chemistry, Section B, Organic Chemistry Including Medicinal Chemistry, vol. 24B, Apr. 1985, pp. 377-382 (In English).

Fomine et al: "Bisimide-Lactamimide . . . " Polymer, Elsevier Publishers B.V., GB, BD. 40, NR. 8., Apr. 1999, pp. 2051-2058 (In English).

Fomine et al: "Synthesis and Characterisation . . . " Macromolecular Chemistry and Physics, Wiley VCH, Weinheim, DE, 200, NR. 1, Jan. 1999, pp. 239-245 (In English).

Fomine S et al: "Tetracarboxylic Bisimide-Lactam . . . " Polymer, Elsevier Science Publishers B.V., GB, vol. 39, No. 25, Dec. 1998, pp. 6415-6421 (In English).

P Ponce et al: "Unusual Behavior of . . . " Journal of Molecular Structure (THEOCHEM) 541, 2001, pp. 131-139 (In English).

P. Ponce et al: "Bisimide-Lactamimide Ring . . . " J. Phys. Org. Chem. 2001, 14, pp. 657-666 (In English).

Langhals, H., et al: "Tetracarboxylic . . . " Angewandte Chem. Ed. Engl., 1995, 34, No. 20, pp. 2234-2236 (In English).

H. Langshals: "Tetracarbonsaeurebisimid-Lactam . . . ", Angew, Chem., 1995, 107, pp. 2436-2439.

* cited by examiner

NAPHTHALENE DERIVATIVES AND COLORANTS FOR KERATIN FIBERS CONTAINING THESE COMPOUNDS

CROSS-REFERENCE

This is the U.S. National Stage of PCT/EP 2004/011853, which was filed on Oct. 20, 2004 in Europe, which, in turn, is based on DE 10 2004 006143.2, which was filed on Feb. 7, 2004, in Germany. The aforesaid German Patent Application provides the basis for a claim of priority of invention for the invention described and claimed herein below in accordance with 35 U.S.C. 119 (a)-(d).

BACKGROUND OF THE INVENTION

The invention has for an object novel uncharged and cationic naphthalene derivatives and colorants for keratin fibers, for example human hair, containing these compounds.

The dyeing of fibrous materials, particularly of keratin-containing fibers, for example hair, wool or furs, is generally carried out either with oxidation dyes formed by oxidative coupling of one or more developer components with one or more coupler components or with direct dyes. If needed, oxidation-resistant direct dyes can be added to the oxidative system to achieve special color effects. Direct dyes are incorporated into appropriate carrier compositions and then applied to the fibers. This process, generally known as tinting, is simple to use and stands out in that it causes only minor damage to the keratin fibers, because the process does not require the use of ammonia or peroxide. The dyes used, however, must meet a few requirements. They must be toxicologically and dermatologically unobjectionable and must make it possible to obtain colorations of the desired intensity and brilliance. Moreover, they must present high resistance to washing, light, perspiration, permanent waving, acids, bases and rubbing. In any event, such hair colorations must remain stable for at least four to six weeks under currently prevailing everyday conditions.

For a direct, nonoxidative colorant for keratin fibers it is usually necessary to use a combination of different nonoxidative dyes to achieve certain color shades. Because the availability of yellow, red and blue dyes that adequately meet all requirements is limited, a great need still exists for such dyes. Another, very interesting application of direct dyes is their use in agents for simultaneous brightening and dyeing. In these dye compositions which can have a higher oxidant content, further requirements are placed on the dyes used, particularly in terms of sufficient resistance to the oxidants used.

SUMMARY OF THE INVENTION

To date, hardly any dyes exist that meet the afore-said requirements and at the same time give satisfactory coloring results. It is an object of the present invention therefore to provide direct dyes for dyeing keratin fibers, particularly human hair, that meet these requirements.

Surprisingly, we have now found that certain novel naphthalene derivatives of general formula (I) can be used as direct dyes both in oxidant-free dye compositions and in brightening dye compositions with higher peroxide and/or persulfate contents. Moreover, the colorants containing the dyes of the invention are superior to common colorants in terms of their dyeing properties.

The present invention therefore has for an object unsymmetrically substituted naphthalene derivatives of general formula (I)

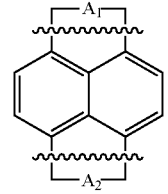

wherein $A_1$ and $A_2$ are different and independently of each other represent partial structures of formulas (II), (IIIa, (IIIb), (IV), (V) or (VI) among which formulas (II), (IIIa), (IIIb), (IV) and (V) are preferred.

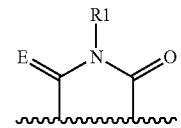

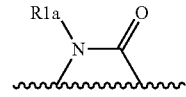

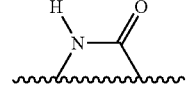

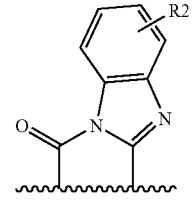

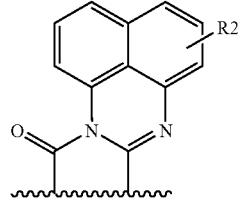

E stands for oxygen or a sulfur atom;

Y stands for a nitrogen atom or (preferably) a quaternary nitrogen atom substituted with branched or linear $C1$-$C_6$-alkyl groups, branched or linear $C_2$-$C_4$-hydroxyalkyl groups or branched or linear $C_4$-$C_6$-polyhydroxyalkyl groups;

$R_1$ denotes a hydrogen atom, an aromatic group or heterocyclic group of general formula (VII), (VIII), (IX), (X), (XI), (XII), (XIII), (XIV), (XV) or (XVI),

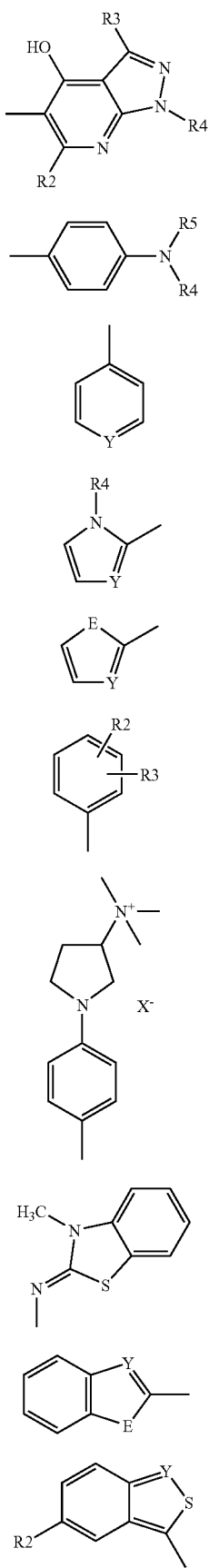

or an aliphatic $C_1$-$C_6$-alkyl group that is linear or branched and is unsubstituted or substituted with one or more hydroxyl groups or with cationic groups of the $B^+$ type;

$R_{1a}$ has the same meaning as $R_1$ with the exception of hydrogen, $R_2$ and $R_3$ can be equal or different and denote hydrogen, an amino group, $C_1$-$C_6$-alkylamino group, a $C_1$-$C_6$—N,N-dialkylamino group, a $C_1$-$C_6$—N,N-(dihydroxyalkyl)amino group, fluorine, chlorine, bromine, iodine, a cyano group, a $C_1$-$C_6$-alkylcyano group, a methoxymethyl group, a tert. butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-hydroxyalkyloxy group, a $C_1$-$C_6$-alkylcarboxylic acid group, a $C_1$-$C_6$-alkylcarboxylate ester group, a $C_1$-$C_6$-alkylcarboxamide group, a $C_1$-$C_6$-alkylsulfonic acid group, a $C_1$-$C_6$-alkyl-sulfonate ester group, a $C_1$-$C_6$-alkylsulfonamide group, a phenyl group, a sulfonic acid group or an -(L)-$B^+$— group;

$R_4$ and $R_5$ can be equal or different and denote hydrogen, a $C_1$-$C_6$-alkylamino group, a $C_1$-$C_6$—N,N-dialkylamino group, a $C_1$-$C_6$-alkylcyano group, a methoxymethyl group, a tert. butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylate ester group, a $C_1$-$C_6$-alkylcarboxamide group, a $C_1$-$C_6$-alkylsulfonic acid group, a $C_1$-$C_6$-alkylsulfonate ester group, a $C_1$-$C_6$-alkylsulfonamide group, a phenyl group or an -(L)-$B^+$— group;

L stands for a $C_1$-$C_6$-alkylene group;

$B^+$ stands for an aromatic heterocyclic quaternary ammonium compound—preferably a quaternary compound of N-methylimidazole, N-allylimidazole, 2-ethylimidazole, 1,2-dimethylimidazole, pyridine, 4-dimethylaminopyridine, pyrimidine, pyrazole, N-methylpyrazole or quinoline; a non-aromatic heterocyclic quaternary ammonium compound—particularly a quaternary compound of N-methylmorpholine, N-ethylmorpholine or 1-methylpiperidine; a quaternary alkylammonium compound or arylammonium compound of formula $NR_aR_bR_c$ wherein $R_a$, $R_b$ and $R_c$ independently of each other denote a benzyl group, a phenyl group or a $C_1$-$C_6$-alkyl group—particularly a methyl, ethyl, propyl, isopropyl or butyl group—the aforesaid alkyl groups possibly being unsubstituted or substituted with one or more hydroxyl groups or amino groups; or a quaternary phosphonium group, for example a tributylphosphonium group, but particularly a trimethylammonium group or a triethylammonium group; and $X^-$ denotes an anion, preferably a sulfate, phosphate, hydrogen phosphate, oxalate, formate, acetate, citrate, tartrate, malonate, pyruvate, chloride, bromide, iodide, or methylsulfate anion, the chloride anion, bromide anion and methylsulfate anion being particularly preferred.

General formula (I) also comprises all possible E- and Z-isomers.

Suitable neutral or cationic naphthalene derivatives of general formula (I) are, for example, the following:

1-(2-tert. butylphenyl)-6-(2-hydroxyethyl)-1H-indolo[5,4,3-def]isoquinoline-2,5,7(6H)-trione, 1-(2-tert. butyl)-6-[2-hydroxy-1-(hydroxymethyl)ethyl-1H-indolo[5,4,3-def]isoquinoline-2,5,7(6H)-trione, 3-{2-[2-(2,5-diketo-5,6-dihydroisoindolo[6,7,1-cde]indol-1(2H)-yl)-5-methoxyanilino]ethyl}-1-methyl-1H-imidazol-3-ium bromide, 3-{2-[4-(2,5-diketo-5,6-dihydroisoindolo[6,7,1-cde]indol-1(2H)-yl)(ethyl)anilino]ethyl}-1-methyl-1H-imidazol-3-ium bromide, 1-{4-[ethyl(2-hydroxyethyl)amino]phenyl}-6-methyl-2,5-diketo-2,5-dihydro-1H-imidazo[1,2-a]isoindolo[6,7,1-def]quinolin-6-ium methylsulfate, 3-{2-[4-(2,5-diketo-2,5-dihydro-1H-imidazol[1,2-a]isoindolo[6,7,1-def]quinolin-1-yl)(ethyl)anilino]-ethyl}-1-methyl-1H-imidazol-3-ium bromide, 1-{2-[(2-hydroxyethyl)amino]-4- methoxyphenyl}-1,6-di-hydroisoindolo[6,7,1-cde]indol-2,5-dione, 1-{4[bis-(2-hydroxyethyl)amino]phenyl}-1,6-dihydroisoindolo-[6,7,1cde]indol-2,5-dione, 3-{2-[1-(tert.butylphenyl)-2,5,7-triketo-1,2,5,7-tetrahydro-6H-indolo-[5,4,3-def]isoquinolin-6-yl]ethyl}-1-methyl-1H-imidazol-3-ium bromide, 3-(2-{1-[4-dimethylamino)phenyl]-2,5,7-triketo-1,2,5,7-tetrahydro-6H-indolo[5,4,3-def]isoquinolin-6-yl}ethyl)-1-methyl-1H-imidazol-3-ium bromide, 2-(4-morpholinyl)benzo[lmn]perimidino[2,1-b][3,8]phenanthrolin-1,3,6-(2H)-trione, 2-[tert. butyl-(2-hydroxyethyl)amino]benzo[lmn]perimidino[2,1-b][3,8]phenanthroline-1,3,6-(2H)-trione, 2-[1-(hydroxymethyl)-2-methylpropyl]benzimidazo[2,1-b]benzo[lmn][3,8]phenanthroline-1,3,6(2H)-trione, 5-methyl-2-(1,3,6-triketo-3,6-dihydrobenzo[lmn]perimidino[2,1-b]-[3,8]phenanthrolin-2(1H)-yl)benzenesulfonic acid and 5-methyl-2-(1,3,6-triketo-3,6-dihydrobenzimidazo[2,1-b]benzo[lmn][3,8]-phenanthrolin-2(1H)-yl)benzenesulfonic acid.

Preferred compounds of general formula (I) are
1-(2-tert. butylphenyl)-6-(2-hydroxyethyl)-1H-indolo[5,4,3-def]isoquinoline-2,5,7(6H)-trione, 1-(2-tert. butyl)-6-[2-hydroxy-1-(hydroxymethyl)ethyl]-1H-indolo[5,4,3-def]isoquinoline-2,5,7(6H)-trione, 3-{2-[2-(2,5-diketo-5,6-dihydroisoindolo[6,7,1-cde]indol-1(2H)-yl)-5-methoxyanilino]ethyl}-1-methyl-1H-imidazol-3-ium bromide, 3-{2-[4-(2,5-diketo-5,6-dihydroisoindolo[6,7,1-cde]indol-1(2H)-yl)(ethyl)anilino]ethyl}-1-methyl-1H-imidazol-3-ium bromide, 3-(2-{1-[4-dimethylamino)phenyl]-2,5,7-triketo-1,2,5,7-tetrahydro-6H-indolo[5,4,3-def]isoquinolin-6-yl}ethyl)-1-methyl-1H-imidazol-3-ium bromide, 2-(4-morpholinyl)benzo[lmn]perimidino[2,1-b][3,8]phenanthroline-1,3,6(2H)-trione, 2-[tert. butyl-(2-hydroxyethyl)amino]benzo[lmn]perimidino[2,1-b][3,8]phenanthroline-1,3,6(2H)-trione, 2-[1-(hydroxymethyl)-2-methylpropyl]benzimidazo[2,1-b]benzo[lmn][3,8]phenanthroline-1,3,6(2H)-trione, 5-methyl-2-(1,3,6-triketo-3,6-dihydrobenzo[lmn]perimidino[2,1-b][3,8-phenanthrolin-2-(1H)-yl)benzenesulfonic acid and 5-methyl-2-(1,3,6-triketo-3,6-dihydrobenzimidazo[2,1-b]benzo[lmn]-[3,8]-phenanthrolin-2(1H)-yl)benzenesulfonic acid.

The naphthalene derivatives of the invention of general formula (I) can be obtained by known methods of synthesis from commercially available or readily prepared components.

The following compounds, for example, can be used as naphthalene precursors: naphthalene-1,8:4,5-tetracarboxylic dianhydride (XVII) and 6-bromonaphthostyryl-5-carboxylic acid (XVIII).

By condensation reactions at elevated temperature in an appropriate solvent, for example glacial acetic acid, DMF or molten imidazole, it is possible to prepare according to Scheme 1 from naphthalene-1,8:4,5-tetracarboxylic dianhydride (XVII) and a primary aliphatic, aromatic or heterocyclic amine or a hydrazone (A1/A2) the corresponding unsymmetrically substituted imides, amidines or isoamidines.

Scheme 1

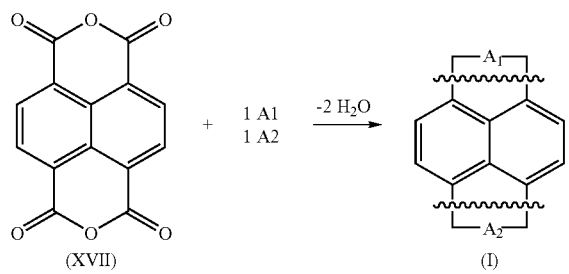

According to H. Langhals et al. (Angew. Chem. 1995, 107; 2436-2439; Angew. Chem., Int. Ed. Engl. 1995 34, 2234-2236) and EP 0 769 532 A1, lactams (XX) can be prepared from any desired diimide derivative (XIX) by a ring-contraction reaction in a DMSO/methanol mixture under strongly alkaline conditions (Scheme 2)

Scheme 2

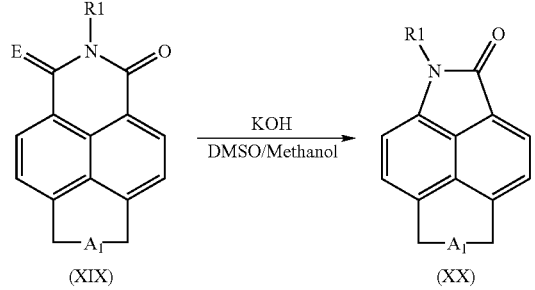

Dilactams (XXI) can be obtained by the Ullmann condensation of aromatic or heterocyclic amines or p-phenylenediamine derivatives (A) with 6-bromonaphthostyryl-5-carboxylic acid (XVIII) as described by S. S. Dalvi et al. (Indian Journal of Chemistry, vol. 24b, April 1985, 377-382).

Scheme 3

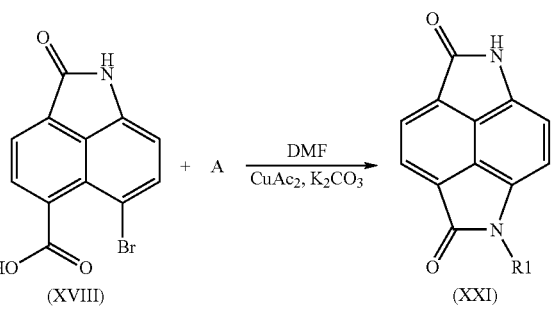

The cationic representatives can be prepared in simple manner by introduction of a cationic group (Scheme 4) or by quaternization of heterocyclic nitrogen atoms (Scheme 5).

Scheme 4

According to Scheme 4, compounds of general formula Q-L-Hal, wherein the Q group stands for a neutral naphthalene derivative of formula (I) and L stands for $C_1$-$C_6$-alkyl (Hal stands for chlorine, bromine or iodine), are made to react by nucleophilic substitution in a dipolar aprotic solvent with compounds of type B, wherein B stands for an aromatic heterocyclic compound—preferably an —N-methylimidazole, N-allylimidazole, 2-ethylimidazole or 1,2-dimethylimidazole, pyridine, 4-dimethylaminopyridine, pyrimidine, pyrazole, N-methylpyrazole or quinoline; or a nonaromatic heterocyclic compound—particularly N-methylmorpholine, N-ethylmorpholine or 1-methylpiperidine; or an alkyl- or aryl compound of formula $NR_aR_bR_c$, wherein $R_a$, $R_b$ and $R_c$ have the afore-indicated meaning and denote, for example a trimethylamino group, triethylamino group or tributylamino group; or a tertiary phosphor-organic group ("tertiary phosphine").

Scheme 5

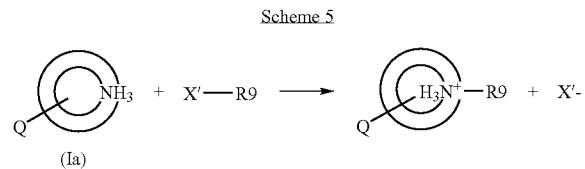

(Ia)

According to Scheme 5, heterocyclic nitrogen atoms in the neutral naphthalene derivatives of formula (Ia) are quaternized with an alkylating agent of general formula $X'$—$R_9$ wherein $X'$ stands for chlorine, bromine, iodine or methylsulfate and $R_9$ stands for a $C_1$-$C_6$-alkyl group, $C_1$-$C_3$-hydroxyalkyl group or $C_4$-$C_6$-polyhydroxyalkyl group.

The novel naphthalene derivatives of general formula (I) make it possible to obtain a uniform, intense and brilliant coloration on fibers, particularly keratin fibers, for example human hair, wool and furs, under gentle and skin-compatible conditions, the colorations showing unusually high resistance to light, perspiration and shampooing. Moreover, with special excitation, for example with UV light, it is possible to observe in some cases pronounced solid-body fluorescence of the dyed fibers.

The invention therefore also has for an object (a) an agent for coloring keratin fibers, particularly human hair, and (b) an agent containing an oxidant for the simultaneous brightening and coloring of keratin fibers, particularly human hair, characterized in that said agent contains at least one naphthalene derivative of general formula (I).

The colorants of the invention contain the naphthalene derivatives of general formula (I) preferably in an amount from 0.01 to 10 weight percent and particularly from 0.1 to 8 weight percent.

Besides the dyes of general formula (I), the colorant (a) of the invention can additionally contain other known direct dyes selected from the group consisting of nitro dyes, azo dyes, anthraquinone dyes and triphenylmethane dyes, alone or in admixture with one another, for example: 1,4-bis-[(2-hydroxyethyl)amino]-2-nitrobenzene, 1-(2-hydroxyethyl)amino-2-nitro-4-[di(2-hydroxyethyl)amino]benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1[(2-hydroxyethyl)amino-2-nitrobenzene hydrochloride (HC Blue No. 12), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)-amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-amino-4-[(2-hydroxyethyl)amino]-2-nitrobenzene (HC Red No. 7), 2-amino-4,6-dinitrophenol, 1,4-diamino-2-nitrobenzene (Cl 76070), 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-2-nitro-1-[(prop-2-en-1-yl)amino]benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 3-amino-6-(methylamino)-2-nitropyridine, 1,2,3,4-tetrahydro-6-nitroquinoxaline, 7-amino-3,4-dihydro-6-nitro-2H-1,4-benzoxazine (HC Red No. 14), 1,2-diamino-4-nitrobenzene (Cl 76020), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)-amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 2,4-dinitro-1-hydroxynaphthalene; 1,4-di[(2,3-dihydroxypropyl)-amino]-9,10-anthraquinone, 1,4-di[(2-hydroxyethyl)amino]-9,10-anthraquinone (Cl 61545, Disperse Blue 23), 1-amino-4-hydroxy-9,10-anthraquinone (Cl 60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-diketo-3,4,6,8-tetrahydroxy-2-anthracenecarboxylic acid (Cl 75470, Natural Red 4), 1-[(3-aminopropyl)amino]-9,10-anthraquinone (HC Red No. 8), 1,4-diamino-9,10-anthraquinone (Cl 61100, Disperse Violet No. 1), 1-amino-4-(methylamino)-9,10-anthraquinone (Cl 61105, Disperse Violet No. 4, Solvent Violet No. 12), N-(6-((3-chloro-4-(methyl-amino)phenyl)imino)-4-methyl-3-keto-1,4-cyclohexadien-1-yl)urea (HC Red No. 9), 2-((4-(di(2-hydroxyethyl)amino)phenyl)amino)-5-((2-hydroxyethyl)amino)-2,5-cyclohexadien-1,4-dione (HC Green No. 1), 2-hydroxy-1,4-naphthoquinone (Cl 75480, Natural Orange No. 6), 1,2-dihydro-2-(1,3-dihydro-3-keto-2H-indol-2-ylidene)-3H-indol-3-one (Cl 73000), 1,3-bis-(dicyanomethylene)indane; di[4-(diethylamino)phenyl][4-(ethylamino)naphthyl]carbenium chloride (Cl 42595; Basic Blue No. 7), di[4-(dimethylamino)phenyl][4-(phenylamino)naphthyl]carbenium chloride (Cl 44045, Basic Blue No. 26), Basic Blue No. 77, 8-amino-2-bromo-5-hydroxy-4-imino-6-[(3-(trimethylammoonio)phenyl)amino]-1(4H)-naphthalinone chloride (Cl 56059, Basic Blue No. 99), tri(4-amino-3-methylphenyl)carbenium chloride (Cl 42520, Basic Violet No. 2), di(4-aminophenyl)(4-amino-3-methylphenyl)carbenium chloride (Cl 42510, Basic Violet No. 14), 1-[(4-aminophenyl)azo]-7-(trimethylammonio)-2-naphthol chloride (Cl 12250. Basic Brown No. 16), 3-[(4-amino-2,5-dimethoxy-phenyl)azo]-N,N,N-trimethylbenzeneaminium chloride (Cl 112605, Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (Cl 12251, Basic Brown No. 17) [sic], 2-((4-aminophenyl)azo]-1,3-dimethyl-1H-imidazol-3-ium chloride (Basic Orange No. 31), 3,7-diamino-2,8-dimethyl-5-phenylphenazinium chloride (Cl 50240, Basic Red No. 2), 1,4-dimethyl-5-[(4-(dimethylamino)phenyl)azo]-1,2,4-triazolium chloride (Cl 11055, Basic Red No. 22), 1,3-dimethyl-2-((4-dimethylamino)phenyl)azo-1H-imidazol-3-ium chloride (Basic Red No. 51), 2-hydroxy-1-[(2-methoxyphenyl)azo]-7-(trimethylammonio)naphthalene chloride (Cl 12245, Basic Red No. 76), 3-methyl-1-phenyl-4-[(3-(trimethylammonio)phenyl)azo]pyrazol-5-one chloride (Cl 12719, Basic Yellow No. 57), 1-methyl-4-((methyl-phenylhydrazono)methyl)pyridinium methylsulfate (Basic Yellow No. 87), 1-(2-morpholiniumpropylamino)-4-hydroxy-9,10-anthraquinone methylsulfate, 1-[(3-(di-methylpropylaminium)propyl)-amino]-4-(methylamino)-9,10-anthraquinone chloride, 1-[di (2-hydroxyethyl)amino]-3-methyl-4-[(4-nitrophenyl)azo] benzene (Cl 11210, Disperse Red No. 17), 1-[di(2-hydroxyethyl)amino]-4-[(4-nitrophenyl)azo]benzene (Disperse Black No. 9), 4-[(4-aminophenyl)-azo]-1-[di(2-hydroxyethyl)amino]-3-methylbenzene (HC Yellow No. 7), 2,6-diamino-3-[(pyridin-3-yl)azo]pyridine and 2-((4-ethyl)-2-hydroxyethyl)amino)-2-methylphenyl)azo)-5-nitro-1,3-thiazole (Cl 111935, Disperse Blue No. 106).

Besides the dyes of general formula (I), the colorant (b) of the invention which additionally contains an oxidant and particularly hydrogen peroxide or a hydrogen peroxide adduct (for example sodium percarbonate or urea peroxide) and/or a persulfate (for example ammonium persulfate, sodium persulfate or potassium persulfate) and/or a perborate, can also contain other known direct dyes resistant to oxidants, for example:

3-(2',6'-diaminopyridyl-3'-azo)pyridine {=2,6-diamino-3-[(pyridin-3-yl)azo]pyridine}, 2-((4-ethyl(2-hydroxyethyl) amino)-2-methylphenyl)azo-5-nitro-1,3-thiazole (Disperse Blue 106), N,N-di(2-hydroxyethyl)-3-methyl-4-[(4-nitrophenyl)azo]aniline (Disperse Red 17, Cl 11210), 3-diethylamino-7-(4-dimethylaminophenylazo)-5-phenylphenazinium chloride (Cl 11050), 4-(2-thiazolylazo)resorcinol, 4-[(4-phenylamino)azo]benzenesulfonic acid sodium salt (Orange IV), 1-[(3-aminopropyl)-amino]-9,10-anthracenedione (HC Red No. 8), 3',3",4,5,5',5",6,7-octabromophenolsulfonaphthalein (Tetrabromophenol Blue), 1-[(4-amino-3,5-dimethylphenyl)-(2,6-dichlorophenyl)methylene]3,5-dimethyl-4-imino-2,5-cyclohexadiene phosphoric acid (1:1) (Basic Blue 77), 3',3",5',5"-tetrabromo-m-cresolsulfonphthalein, 2,4-dinitro-1-naphthol-7-sulfonic acid disodium salt (Acid Yellow 1, Cl 10316), 4-[2'-hydroxy-1'-naphthyl)azo] benzenesulfonic acid sodium salt (Acid Orange 7, Cl 15510), 3',6'-dihydroxy-2',4',5',7'-tetraiodispiro[isobenzofuran-1 (3H),9'(9H)xanthan]-3-one disodium salt (Acid Red 51, Cl 45430), 6-hydroxy-5-[(2-methoxy-5-methyl-4-sulfophenyl) azo]-2-naphthalenesulfonic acid disodium salt (FD&C Red No. 40, Cl 16035), 2,4-dinitro-1-naphthol sodium salt (Acid Yellow 24, Cl 10315), 2',4',5',7'-tetrabromo-4,5,6,7-tetrachloro-3',6'-dihydroxyspiro[isobenzofuran-1(3H),9'(9H) xanthen]-3-one disodium salt (Acid Red 92, Cl 45410), 4-(2-hydroxy-1-naphthylazo)-3-methylbenzenesulfonic acid sodium salt (Acid Orange 8, Cl 15575), 2-amino-1,4-naphthalenedione, dithizone (1,5-diphenylthiocarbazone), N-(2-hydroxyethyl)-2-nitro-4-trifluoromethyl)aniline (HC Yellow 13), N-(2-hydroxyethyl)-4-nitroaniline and 4-chloro-N-(2,3-dihydroxypropyl)-2-nitroaniline.

The agent of the invention can contain the afore-said additional direct dyes in a total amount of about 0.01 to 4 weight percent, the total amount of dyes in the colorant of the invention preferably being about 0.01 to 10 weight percent and particularly 0.1 to 5 weight percent.

Furthermore, the colorant of the invention can contain all common additives known to be used in such preparations, for example perfume oils, complexing agents, waxes, preservatives, thickeners, alginates, guar gum, hair-care substances, for example cationic polymers or lanolin derivatives, or anionic, nonionic, amphoteric or cationic surface-active substances. Preferably used are amphoteric or nonionic substances, for example betaine surfactants, propionates and glycinates, for example cocoamphoglycinates or cocoamphodiglycinates, ethoxylated surfactants with 1 to 1000 ethylene oxide units and preferably with 1 to 300 ethylene oxide units, for example glyceride alkoxylates, for example with 25 ethylene oxide units, ethoxylated castor oil, polyethylene glycol amides, ethoxylated alcohols and ethoxylated fatty alcohols (fatty alcohol alkoxylates) and ethoxylated sugar esters of fatty acid, particularly ethoxylated sorbitan fatty acid esters. The afore-said constituents are used in amounts commonly employed for such purposes, for example the surface-active substances at a concentration of 0.1 to 30 weight percent, and the hair-care agents in an amount from 0.1 to 5 weight percent. The colorant of the invention, particularly when it is a hair colorant, can be in the form of an aqueous or aqueous-alcoholic solution, a cream, gel, emulsion or aerosol foam. The hair colorant can be in the form of a one-component preparation or in the form of a multicomponent preparation, for example in the form of a two-component preparation in which the dye derivative of general formula (I) is packaged separately from the other constituents, and the ready-to-use hair colorant is prepared just before use by mixing the two components. When the dyes are to be used together with an oxidant, the colorant can also be packaged in the form of a 2-component preparation in which one component is the oxidant and the other component contains the other constituents, the oxidant optionally also consisting of several components (for example 1. hydrogen peroxide and 2. persulfate).

The colorant of the invention has a pH of about 2 to 10, preferably of about 5 to 10 and particularly a neutral to basic pH of about 7 to 10. Organic and inorganic acids and bases are suitable for pH adjustment. Suitable acids are, in particular, α-hydroxycarboxylic acids, for example glycolic acid, lactic acid, tartaric acid, citric acid or malic acid, ascorbic acid, glucuronolactone, acetic acid, hydrochloric acid or phosphoric acid as well as mixtures of these acids. Suitable bases are, in particular, sodium carbonate, sodium hydrogen carbonate, alkanolamines, for example monoethanolamine or triethanolamine, ammonia, aminomethylpropanol and sodium hydroxide.

The colorant of the invention is normally used by applying to the fibers an amount thereof sufficient for the dyeing, usually about 30 to 120 grams (optionally with addition of a suitable oxidant). The colorant is then allowed to act at about 5 to 45° C. for about 1 to 60 minutes and preferably for 5 to 30 minutes, after which the fibers are thoroughly rinsed with water, optionally washed with a shampoo and then dried.

Moreover, if no oxidant is added to the dye composition, the afore-described colorant can contain natural or synthetic polymers or modified polymers of natural origin commonly used in cosmetic agents whereby the hair is fixed at the same time it is dyed. Such agents are generally referred to as tint fixatives or dye fixatives.

Synthetic polymers that are known to be used for this purpose in the cosmetic field are, for example, polyvinylpyrrolidone, polyvinyl acetate, polyvinyl alcohol or polyacrylate compounds such as polyacrylic acid or polymethacrylic acid, basic polymers of esters of polyacrylic acid or polymethacrylic acid and aminoalcohols, for example the salts or quaternization products thereof, polyacrylonitrile, polyvinyl acetate, as well as the copolymers of such compounds, for example polyvinyl-pyrrolidone-vinyl acetate, whereas suitable natural polymers or modified natural polymers are, for example, chitosan (deacetylated chitin) or chitosan derivatives.

The afore-said polymers can be contained in the colorant of the invention in amounts commonly employed in such cosmetic agents, particularly in an amount from about 1 to 5 weight percent. The pH of the tint fixative or dye fixative of the invention is preferably about 6 to 9.

The colorant additionally providing hair firming is used in the known and usual manner by moistening the hair with the firming agent, arranging (styling) the hair into a hairdo and then drying.

The colorant of the invention imparts to keratin fibers (for example human hair, wool or furs) an outstanding, uniform, intense and very durable coloration without appreciably staining the skin or the scalp, a coloration capable of withstanding five or more hair washings without an appreciable fading of the hair color.

The following examples will explain the subject matter of the invention without limiting it to the examples.

EXAMPLES

Example 1

Preparation of 1-(2-tert. butylphenyl)-6-(2-hydroxyethyl)-1H-indolo[5,4,3def]isoquinoline-2,5,7(6H)-trione Step 1:

Preparation of 2-(2-tert. butylphenyl)-6-(2-hydroxyethyl)-7-(2-hydroxyethyl)-benzo-[lmn]-[3,8]phenanthroline-1,3,6,8-(2H,7H)-tetrone 3.0 g (11.19 mmol) of naphthalene-1,8:4,5-tetracarboxylic dianhydride was mixed with 8 g of imidazole and stirred at 150° C. To this mixture were added slowly and dropwise in alternating fashion and with the aid of an injection needle 2.0 g (13.24 mmol) of 2-tert. butylaniline and 0.82 g (13.43 mmol) of ethanolamine. After 2.5 hours, the mixture was poured into 2N hydrochloric acid and stirred overnight. The precipitate was filtered off and dried. The resulting crude product was used in Step 2 directly without further purification.

Step 2:

Preparation of 1-(2-tert. butylphenyl)-6-(2-hydroxyethyl)-1H-indolo[5,4,3def]isoquinoline-2,5,7(6H)-trione 1.7 g (3.84 mmol) of 2-(2-tert. butylphenyl)-7-(2-hydroxyethyl)benzo[lmn]-[3,8-phenathroline-1,3,6,8(2H,7H)-tetrone from Step 1 was dissolved in a mixture of 40 mL of DMSO and 20 mL of methanol. Then, 6.46 g (115.2 mmol) of finely pulverized potassium hydroxide was added, and the mixture was heated at the boil for 3 hours. After cooling, the dark-red solution was poured into 2N hydrochloric acid and allowed to stand overnight. The yellow precipitate was filtered off, washed with water and dried. The purification was carried out chromatographically over silica gel with toluene/ethanol 10:1 as the developing solvent.

Yield: 0.92 g (58% of the theoretical), dark-yellow powder.
$^1$H-NMR (d$_6$-DMSO/300 MHz): δ=1.31 (s, 9H, tert. butyl), 2.06 (s, 1H, OH), 3.69 (t, J=14.4 Hz, 2H, ethyl), 4.65 (t, J=14.4 Hz, 2H, ethyl), 6.71 (d, J=7.5 Hz, 1H, naphthalene), 7.11 (d, J=9.3 Hz, 1H, phenyl), 7.36-7.43 (m, 1H, phenyl), 7.49-7.54 (m, 1H, phenyl), 7.70 (d, J=9.3 Hz, 1H, phenyl), 8.29 (d, J=7.2 Hz, 1H, naphthalene), 8.44 (d, J=7.2 Hz, 1H, naphthalene), 8.91 (d, J=7.5 Hz, 1H, naphthalene).

Example 2

Preparation of 3-{2-[1-(2-tert. butylphenyl)-2,5,7-triketo-1,2,5,7-tetrahydro-6H-indolo-[5,4,3-def]isoquinolin-6-yl]ethyl}-1-methyl-1H-imidazol-3-ium bromide Step 1:

Preparation of 1-(2-tert. butylphenyl)-6-(2-bromoethyl)-1H-indolo[5,4,3-def]isoquinoline-2,5,7(6H)-trione 0.92 g (2.22 mmol) of 1-(2-tert. butylphenyl)-6-(2-hydroxyethyl)-1H-indolo[5,4,3-def]isoquinoline-2,5,7(6H)-trione was dissolved in 60 mL of chloroform and heated to a boil. Then, 15 mL (15.54 mmol) of phosphorus tribromide was added dropwise within 20 minutes and the solution was heated at reflux for 2 hours. The reaction mixture was then poured onto ice, and the aqueous phase was extracted with chloroform. The combined organic phases were dried over magnesium sulfate. The purification was carried out by column chromatography on silica gel with toluene as the developing solvent.

Yield: 0.51 g (48% of the theoretical), light-yellow powder.
$^1$H-NMR (d$_6$-DMSO/300 MHz): δ=1.33 (s, 9H, tert. butyl), 3.68 (t, J=14.4 Hz, 2H, ethyl), 4.63 (t, J=14.4 Hz, 2H, ethyl), 6.74 (d, J=7.5 Hz, 1H, naphthalene), 7.14 (d, J=9.3 Hz, 1H, phenyl), 7.39-7.42 (m, 1H,phenyl), 7.50-7.55 (m, 1H, phenyl), 7.72 (d, J=9.3 Hz, 1H, phenyl), 8.30 (d, J=7.2 Hz, 1H, naphthalene), 8.42 (d, J=7.2 Hz, 1H, naphthalene), 8.89 (d, J=7.5 Hz, 1H, naphthalene).

Step 2:

Preparation of 3-{2-[1-(2-tert. butylphenyl)-2,5,7-triketo-1,2,5,7-tetrahydro-6H-indolo-[5,4,3-def]isoquinolin-6-yl]ethyl}-1-methyl-1H-imidazol-3-ium bromide 0.40 g (0.84 mmol) of 1-(2-tert. butylphenyl)-6-(2-bromoethyl)-1H-indolo[5,4,3-def]isoquinoline-2,5,7(6H)-trione from Step 1 was dissolved in 40 mL of acetonitrile. After adding 0.35 g (4.20 mmol) of N-methylimidazole, the mixture was stirred at reflux for 2 hours. After removing the solvent, the precipitate was filtered off, washed with ethyl acetate and dried.

Yield: 0.36 g (77% of the theoretical), orange-yellow powder UV/Vis(DMSO): $\lambda_{max}$=362, 432 nm.

Example 3

Preparation of 2-(4-morpholinyl)benzo[lmn]perimidino[2,1-b][3,8]-phenanthroline-1,3,6(2H)-trione The product was obtained as a dark-blue powder by condensation of 1.68 g (16.42 mmol) of N-aminomorpholine and 2.60 g (16.42 mmol) of 1,8-diaminonaphthalene with 4.00 g (14.92 mmol) of naphthalene-1,8:4,5-tetracarboxylic dianhydride in 30 g of molten imidazole (synthesis and work-up as in Example 1, Step 1) followed by chromatographic purification on silica gel with toluene and acetone as the developing solvents.

Yield: 1.57 g (23% of the theoretical), dark-blue powder UV/Vis(CHCl$_3$): $\lambda_{max}$=358, 377, 589 nm.

Example 4

Preparation of 2-[tert. butyl-(2-hydroxyethyl)amino] benzo[lmn]perimidino-[2,1-b][3,8]phenanthroline-1,3,6(2H)-trione The product was obtained as a dark-blue powder by condensation of 1.63 g (12.30 mmol) of N-tert. butyl-N-hydroxyethylhydrazine and 1.95 g (12.30 mmol) of 1,8-diaminonaphthalene with 3.00 g (11.18 mmol) of naphthalene-1,8:4,5-tetracarboxylic dianhydride in 20 g of molten imidazole (synthesis and work-up as in Example 1, Step 1). The purification was carried out by column chromatography on silica gel with toluene/ethyl acetate as the developing solvent.

Yield: 2.14 g (38% of the theoretical), dark-blue powder UV/Vis(CHCl$_3$): $\lambda_{max}$=sh 365, 376, 581 nm.

Example 5

Preparation of 2-[1-(hydroxymethyl)-2-methylpropyl]benzimidazo[2,1-b]benzo[lmn]-[3,8]-phenanthroline-1,3,6(2H)-trione The product was obtained as a dark-yellow powder by condensation of 0.85 g (8.21 mmol) of 2-amino-1-hydroxy-3-methylbutane (L-valinol) and 0.89 g (8.21 mmol) of 1,2-diaminobenzene with 2.00 g (7.46 mmol) of naphthalene-1,8:4,5-tetracarboxylic acid dianhydride in molten imidazole (synthesis and work-up as in Example 1, Step 1). The product was further purified by filtration over silica gel with the aid of a methylene chloride/ethanol mixture.

Yield: 1.99 g (63% of the theoretical), dark-yellow powder UV/Vis(CHCl$_3$): $\lambda_{max}$=300, 312, 371, 437 nm.

Example 6

Preparation of 5-methyl-2-(1,3,6-triketo-3,6-dihydrobenzo[lmn]perimidino-[2,1-b][3,8]phenanthrolin-2(1H)-yl)benzenesulfonic acid 1.54 g (8.20 mmol) of 2-amino-5-methylbenzenesulfonic acid and 1.30 g (8.20 mmol) of 1,8-diaminonaphthalene were made to react with 2.00 g (7.46 mmol) of naphthalene-1,8:4,5-tetracarboxylic dianhydride in 15 g of molten imidazole 170° C. After 3 hours, the reaction was discontinued and the mixture was poured into ethanol. The resulting violet suspension was stirred for an additional hour and then allowed to stand overnight in a refrigerator. The precipitate formed upon addition of potassium acetate was filtered off, washed portionwise with acetone, taken up in a small amount of N,N-dimethylacetamide and then filtered to remove excess potassium acetate. Evaporation of the violet solution gave the product as a blue powder.

Yield: 3.45 g (83% of the theoretical), dark-blue powder UV/Vis(DMSO): $\lambda_{max}$=362, 382, 576 nm.

Example 7

Preparation of 5-methyl-2-(1,3,6-triketo-3,6-dihydrobenzimidazo-[2,1-b]benzo[lmn][3,8]-phenantholin-2(1H)-yl)benzenesulfonic acid 0.89 g (8.20 mmol) of 1,2-diaminobenzene and 1.54 g (8.20 mmol) of 2-amino-5-methylbenzene-sulfonic acid were made to react with 2.00 g (7.46 mmol) of naphthalene-1,8:4,5-tetracarboxylic dianhydride in 15 g of molten imidazole at 170° C. After 4 hours, the mixture was poured into ethanol. The resulting red suspension was stirred for an additional hour and then allowed to stand overnight in a refrigerator. Further purification was carried out as in Example 6. The resulting crude product was then subjected to extraction with methylene chloride to remove additional impurities. The extraction residue was washed with a small amount of acetone and then dried. This gave the product as a red powder.

Yield: 2.88 g (76% of the theoretical), red powder UV/Vis (DMSO): $\lambda_{max}$=361, 382, 433, 534 nm.

Example 8

Hair Colorant (Without Oxidant)

| | |
|---|---|
| 2.5 mmol | of the naphthalene derivative of general formula (l) |
| 5.0 g | of ethanol |
| 4.0 g | of decylpolyglucose |
| 0.2 g | of disodium ethylenediaminetetraacetate hydrate |
| to 100.0 g | water, demineralized |

The coloring solution was adjusted to pH 7 to 10 by addition of ammonia.

The hair was colored by applying to it an amount of the colorant sufficient for hair coloring. After an exposure time of 30 minutes at 40° C., the hair was rinsed with lukewarm water and then dried. The coloring results are summarized in the following Table 1.

Example 9

Hair Colorant (Without Oxidant)

| | |
|---|---|
| 2.5 mmol | of the naphthalene derivative of general formula (l) |
| 1.3 g | of citric acid, anhydrous |
| 25.0 g | of ethanol |
| 10.0 g | of 1,2-propanediol |
| 9.0 g | of benzyl alcohol |
| 4.0 g | of hydroxyethylcellulose |
| to 100.0 g | water, demineralized |

The hair was colored by applying to it an amount of the colorant sufficient for hair coloring. After an exposure time of 30 minutes at 40° C., the hair was rinsed with lukewarm water and then dried. The coloring results are summarized in the following Table 1.

Example 10

Hair Colorant (With Oxidant)

| | |
|---|---|
| 0.100 g | of the naphthalene derivative of general formula (l) |
| 1.000 g | of potassium persulfate |
| 1.500 | of ammonium persulfate |
| 1.200 g | of sodium silicate |
| 0.625 g | of magnesium oxide |
| 0.250 g | of hydroxyethylcellulose |
| 0.300 g | of granular soap |
| 0.100 g | of disperse silicic acid |
| 0.025 g | of disodium EDTA |
| 10.000 g | of hydrogen peroxide (12% in water) |

The foregoing components were blended into a uniform mixture so that no dye particles could be seen. Then an amount of the afore-said colorant sufficient for hair coloring was applied to the hair. After an exposure time of 45 minutes at 40° C., the hair was rinsed with lukewarm water, treated with an acidic conditioner, again rinsed and dried. The coloring results are summarized in the following Table 1.

TABLE 1

| Example No. | Dye of General Formula (I) | Coloration |
|---|---|---|
| 8 | 3-{2-[1-(2-tert. butylphenyl)-2,5,7-triketo-1,2,5,7-tetrahydro-6H-indolo[5,4,3-def]isoquinolin-6-yl]-ethyl}-1-methyl-1H-imidazol-3-ium bromide | orange-red |
| 9 | 5-methyl-2-{1,3,6-triketo-3,6-dihydrobenzimidazo[2,1-b]-benzo[lmn][3,8]-phenanthrolin-2(1H)-yl}benzenesulfonic acid | orange |
| 10 | 1-(2-tert. butylphenyl)-6-(2-hydroxyethyl)-1H-indolo-[5,4,3-def]isoquinoline-2,5,7(6H)-trione | orange-yellow |

Example 11

Hair Colorant (With Oxidant and Additional Direct Dye)

| | |
|---|---|
| 0.100 g | of 1-(2-tert. butylphenyl)-6-(2-hydroxyethyl)-1H indolo [5,4,3,def]-isoquinoline-2,5,7(6H)-trione |
| 0.050 g | of 3',3'',4,5,5',5'',6,7-octabromophenolsulfonaphthalein (Tetrabromophenol Blue) |
| 1.000 g | of potassium persulfate |
| 1.500 g | of ammonium persulfate |
| 1.200 g | of sodium silicate |
| 0.625 g | of magnesium oxide |
| 0.250 g | of hydroxyethylcellulose |
| 0.300 g | of granular soap |
| 0.100 g | of disperse silicic acid |
| 0.025 g | of disodium EDTA |
| 10.000 g | of hydrogen peroxide (12% in water) |

The foregoing components were blended into a uniform mixture so that no dye particles could be seen. An amount of the afore-said colorant sufficient for hair coloring was then applied to the hair. After an exposure time of 45 minutes at 40° C., the hair was rinsed with lukewarm water and dried. This gave a turquoise coloration.

Example 12

Hair Colorant (with Oxidant and Additional Direct Dye)

| | |
|---|---|
| 0.100 g | of 1-(2-tert. butylphenyl)-6-(2-hydroxyethyl)-1H indolo [5,4,3,def]-isoquinoline-2,5,7(6H)-trione |
| 0.050 g | of 2',4',5',7'-tetrabromo-4,5,6,7-tetrachloro-3',6'-dihydroxyspiro[isobenzofuran-1(3H),9'(9H)xanthen]-3-one disodium salt (Acid Red 92; Cl 45410) |
| 1.000 g | of potassium persulfate |
| 1.500 g | of ammonium persulfate |
| 1.200 g | of sodium silicate |
| 0.625 g | of magnesium oxide |
| 0.250 g | of hydroxyethylcellulose |
| 0.300 g | of granular soap |
| 0.100 g | of disperse silicic acid |
| 0.025 g | of disodium EDTA |
| 10.000 g | of hydrogen peroxide (12% in water) |

The foregoing components were blended into a uniform mixture so that no dye particles could be seen. An amount of the afore-said colorant sufficient for hair coloring was then applied to the hair. After an exposure time of 45 minutes at 40° C., the hair was rinsed with lukewarm water and dried. This gave a light-red coloration.

Unless otherwise indicated, all percentages given in the present patent application are by weight.

The invention claimed is:

1. An agent for coloring keratin fibers, said agent containing at least one cosmetic ingredient selected from the group consisting of oxidants, perfume oils, complexing agents, waxes, preservatives, thickeners, alginates, guar gum, lanolin derivatives, anionic surface-active substances, cationic surface-active substances, nonionic surface-active substances, amphoteric surface-active substances, natural polymers, synthetic polymers, modified polymers of natural origin, nitro dyes, azo dyes, anthraquinone dyes and triphenylmethane dyes; and at least one naphthalene derivative of formula (I):

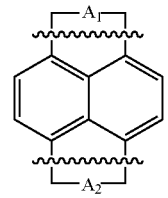

(I)

wherein $A_1$ and $A_2$ are different from each other and, independently of each other, each denote a partial structure of formula (II), (IIIa), (IIIb), (IV), (V), or (VI):

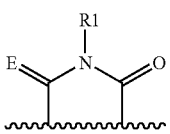

(II)

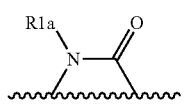

(IIIa)

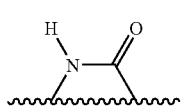

(IIIb)

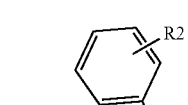

(IV)

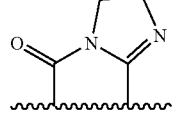

(V)

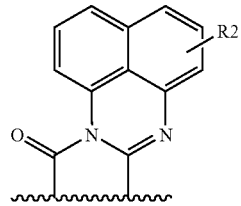

-continued

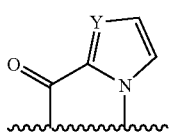
(VI)

E denotes oxygen or a sulfur atom;
Y denotes a nitrogen atom or a quaternary nitrogen atom substituted with branched or linear $C_1$-$C_6$-alkyl groups, branched or linear $C_2$-$C_4$-hydroxyalkyl groups or branched or linear $C_4$-$C_6$-polyhydroxyalkyl groups;
$R_1$ denotes a hydrogen atom, an aromatic or heterocyclic group of general formula (VII), (VIII), (IX), (X), (XI), (XII), (XIII), (XIV), (XV) or (XVI),

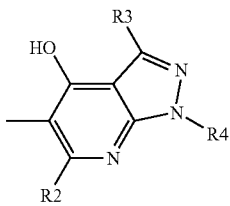
(VII)

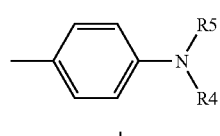
(VIII)

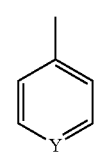
(IX)

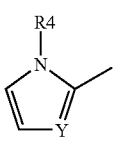
(X)

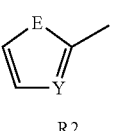
(XI)

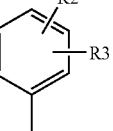
(XII)

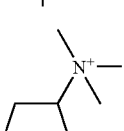
(XIII)

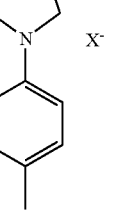

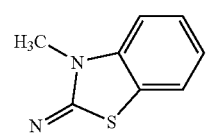
(XIV)

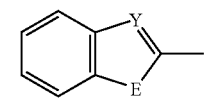
(XV)

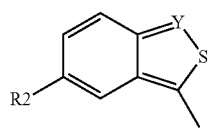
(XVI)

or an aliphatic $C_1$-$C_6$-alkyl group that is linear or branched and is unsubstitued or substituted with one or more hydroxyl groups or with cationic groups of a $B^+$ type;

$R_{1a}$ has the same meaning as $R_1$, except that $R_{1a}$ is not hydrogen;

$R_2$ and $R_3$ are the same or different and, independently of each other, each denote hydrogen, an amino group, a $C_1$-$C_6$-alkylamino group, a $C_1$-$C_6$-N, N-dialkylamino group, a $C_1$-$C_6$—N,N-(dihydroxyalkyl)-amino group, fluorine, chlorine, bromine, iodine, a cyano group, a $C_1$-$C_6$-alkylcyano group, a methoxymethyl group, a tert.-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-hydroxyalkyloxy group, a $C_1$-$C_6$-alkyl-carboxylic acid group, a $C_1$-$C_6$-alkylcarboxylate ester group, a $C_1$-$C_6$-alkylcarboxamide group, a $C_1$-$C_6$-alkylsulfonic acid group, a $C_1$-$C_6$-alkysulfonate ester group, a $C_1$-$C_6$-alkylsulfonamide group, a phenyl group, a sulfonic acid group or an -(L)-$B^+$ group;

$R_4$ and $R_5$ are the same or different and, independently of each other, each denote hydrogen, a $C_1$-$C_6$-alkylamino group, a $C_1$-$C_6$N,N-dialkylamino group, a $C_1$-$C_6$-alkylcyano group, a methoxymethyl group, a tert. butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylate ester group, a $C_1$-$C_6$-alkylcarboxamide group, a $C_1$-$C_6$-alkylsulfonic acid group, a $C_1$-$C_6$-alkylsulfonate ester group, a $C_1$-$C_6$-alkylsulfonamide group, a phenyl group or an -(L)-$B^+$ group;

L stands for a $C_1$-$C_6$-alkylene group;

$B^+$ denotes an aromatic heterocyclic quaternary ammonium compound, a nonaromatic heterocyclic quaternary ammonium compound, a quaternary alkylammonium compound or an arylammonium compound of formula $NR_aR_bR_c$, wherein $R_a$, $R_b$ and $R_c$, independently of each other, denote a benzyl group, a phenyl group or a $C_1$-$C_6$-alkyl group, wherein said alkyl groups are unsubstituted or substituted with one or more hydroxyl groups or with one or more amino groups; or $B^+$ denotes a quaternary phosphonium group; and $X^-$ denotes an anion.

2. The agent as defined in claim 1, wherein said at least one naphthalene derivative of formula (I) is selected from the group consisting of 1-(2-tert.-butylphenyl)-6-(2-hydroxyethyl)-1H-indolo[5,4,3-def]isoquinoline-2,5,7(6H)-trione, 1-(2-tert. butylphenyl)-6-[2-hydroxy-1-(hydroxymethyl) ethyl]-1H-indolo[5,4,3-def]-isoquinoline-2,5,7(6H)-trione, 3-{2-[2-(2,5-diketo-5,6-dihydroisoindolo[6,7,1-cde]indol-1

(2H)-yl)-5-methoxyanilino]ethyl}-1-methyl-1H-imidazol-3-ium bromide, 3-{2-[4-(2,5-diketo-5,6-dihydroisoindolo-[6,7,1-cde]indol-1(2H)-yl)(ethyl)anilino]ethyl}-1-methyl-1H-imidazol-3-ium bromide, 1-{4-[ethyl(2-hydroxyethyl)amino]phenyl}-6-methyl-2,5-diketo-2,5-dihydro-1H-imidazo[1,2-a]isoindolo[6,7,1-def]quinolin-6-ium methyl sulfate, 3-{2-[4-(2,5-diketo-2,5-dihydro-1-H-imidazol[1,2-a]isoindolo[6,7,1-def]-quinolin-1-yl)(ethyl)anilino]ethyl}-1-methyl-1H-imidazol-3-ium bromide, 1-{2-[(2-hydroxy-ethyl)-amino]-4-methoxyphenyl}-1,6-dihydroisoindolo[6,7,1-cde]indole-2,5-dione, 1-{4[bis-(2-hydroxyethyl)amino]phenyl}-1,6-dihydroisoindolo[6,7,1 cde]-indol-2,5-dione, 3-{2-[1-(2-tert.-butylphenyl)-2,5,7-triketo-1,2,5,7-tetrahydro-6H-indolo-[5,4,3-def]isoquinolin-6-yl]ethyl}-1-methyl-1H-imidazol-3-ium bromide, 3-(2-{1-[4-(dimethylamino)phenyl]-2,5,7-triketo-1,2,5,7-tetrahydro-6H-indolo-[5,4,3-def[-isoquinolin-6-yl}ethyl)-1-methyl-1H-imidazol-3-ium bromide, 2-(4-morpholinyl)benzo[lmn]perimidino[2,1-b][3,8]-phenanthroline-1,3,6-(2H)-trione, 2-[tert.-butyl-(2-hydroxyethyl)amino]benzo[lmn]-perimidino-[2,1-b]-[3,8] phenanthroline-1,3,6(2H)-trione, 2-[1-(hydroxymethyl)-2-methylpropyl]-benzimidazo[2,1-b]benzo[lmn]-[3,8] phenanthroline-1,3,6[2H]-trione, 5-methyl-2-(1,3,6-triketo-3,6-dihydrobenzo[lmn]perimidino-[2,1-b][3,8]-phenanthrolin-2(1H)-yl)-benzene sulfonic acid and 5-methyl-2-(1,3,6-triketo-3,6-dihydrobenzimidazo[2,1-b]benzo[lmn][3,8[-phenanthroline-2(1H)-yl)benzene sulfonic acid.

3. The agent as defined in claim 1, wherein said at least one naphthalene derivative of formula (I) is selected from the group consisting of 1-(2-tert.-butyl-phenyl)-6-(2-hydroxy-ethyl)-1H-indolo[5,4,3-def]-isoquinoline-2,5,7(6H)-trione, 1-(2-tert.-butyl)-6-[2-hydroxy-1-(hydroxymethyl)ethyl]-1H-indolo-[5,4,3-[def]-isoquinolin-2,5,7(6H)-trione, 3-{2-[2-(2,5-diketo-5,6-dihydroisoindolo-[6,7,1-cde]-indol-1 (2H)-yl)-5-methoxyanilino]ethyl}-1-methyl-1H-imidazol-3-ium bromide, 3-{2-[4-(2,5-diketo-5,6-dihydroisoindolo[6,7,1-cde]indol-1(2H)-yl)(ethyl)anilino]-ethyl}-1-methyl-1H-imidazol-3-ium bromide, 3-(2-{1-[4-(dimethylamino)phenyl]-2,5,7-triketo-1,2,5,7-tetrahydro-6H-indolo[5,4,3-def]isoquinolin-6-yl}ethyl)-1-methyl-1H-imidazol-3-ium bromide, 2-(4-morpholinyl)benzo[lmn]perimidino-[2,1-b]-[3,8]-phenanthroline-1,3,6-(2H)-trione, 2-[tert.-butyl-(2-hydroxyethyl)-amino]-benzo[lmn]-perimidino-[2,1-b][3,8]-phenanthroline-1,3,6(2H)-trione, 2-[1-(hydroxymethyl)-2-methylpropyl]benzimidazo[2,1-b]-benzo-[lmn][3,8]-phenanthroline-1,3,6[2H]-trione, 5-methyl-2-(1,3,6-triketo-3,6-dihydrobenzo-[lmn]perimidino[2,1-b][3,8]-phenanthrolin-2(1H)-yl)benzene sulfonic acid and 5-methyl-2-(1,3,6-triketo-3,6-di-hydrobenzimidazo[2,1-b]benzo[lmn][3,8]-phenanthrolin-2(1H)-yl)benzene sulfonic acid.

4. The agent as defined in claim 1, wherein said oxidants comprise hydrogen peroxide, hydrogen peroxide adducts, persulfates, and perborates.

5. The agent as defined in claim 1, containing from 0.01 to 10 weight percent of said at least one naphthalene derivative of the formula (I).

6. The agent as defined in claim 1, consisting of a hair colorant.

7. The agent as defined in claim 1, wherein said Y is said quaternary nitrogen atom substituted with said branched or linear $C_1$-$C_6$-alkyl groups, said branched or linear $C_2$-$C_4$-hydroxyalkyl groups or said branched or linear $C_4$-$C_6$-polyhydroxyalkyl groups.

8. The agent as defined in claim 1, wherein said $A_1$ and said $A_2$ each denote said partial structure of the formula (II), (IIIa), (IIIb), (IV), or (V).

9. A naphthalene derivative compound selected the group consisting of 1-(2-tert.-butylphenyl)-6-(2-hydroxyethyl)-1H-indolo[5,4,3-def]isoquinoline-2,5,7(6H)-trione, 1-(2-tert. butylphenyl)-6-[2-hydroxy-1-(hydroxymethyl)ethyl]-1H-indolo[5,4,3-def]-isoquinoline-2,5,7(6H)-trione, 3-{2-[2-(2,5-diketo-5,6-dihydroisoindolo[6,7,1-cde]indol-1(2H)-yl)-5-methoxyanilino]ethyl}-1-methyl-1H-imidazol-3-ium bromide, 3-{2-[4-(2,5-diketo-5,6-dihydroisoindolo-[6,7,1-cde]indol-1(2H)-yl)(ethyl)anilino]ethyl}-1-methyl-1H-imidazol-3-ium bromide, 1-{4-[ethyl(2-hydroxyethyl)amino]phenyl}-6-methyl-2,5-diketo-2,5-dihydro-1H-imidazo[1,2-a]isoindolo[6,7,1-def]quinolin-6-ium methyl sulfate, 3-{2-[4-(2,5-diketo-2,5-dihydro-1H-imidazol[1,2-a]isoindolo[6,7,1-def]-quinolin -1-yl)(ethyl)anilino]ethyl}-1-methyl-1H-imidazol-3-ium bromide, 1-{2-[(2-hydroxy-ethyl)-amino]-4-methoxyphenyl}-1,6-dihydroisoindolo[6,7,1-cde]indole-2,5-dione, 1-{4[bis-(2-hydroxyethyl)amino]phenyl}-1,6-dihydroisoindolo[6,7,1cde]-indol-2,5-dione, 3-{2-[1-(2-tert.-butylphenyl)-2,5,7-triketo-1,2,5,7-tetrahydro-6H-indolo-[5,4,3-def]isoquinolin-6-yl]ethyl}-1-methyl-1H-imidazol-3-ium bromide, 3-(2-{1-[4-(dimethylamino)phenyl]-2,5,7-triketo-1,2,5,7-tetrahydro-6H-indolo-[5,4,3-def]-isoquinolin-6-yl}ethyl)-1-methyl-1H-imidazol-3-ium bromide, 2-(4-morpholinyl)benzo[lmn]perimidino[2,1-b][3,8]-phenanthroline-1,3,6-(2H)-trione, 2-[tert.-butyl-(2-hydroxyethyl)amino]benzo[lmn]-perimidino-[2,1-b]-[3,8] phenanthroline-1,3,6(2H)-trione, 2-[1-(hydroxymethyl)-2-methylpropyl]-benzimidazo[2,1-b]benzo[lmn]-[3,8] phenanthroline-1,3,6[2H]-trione, 5-methyl-2-(1,3,6-triketo-3,6-dihydrobenzo[lmn]perimidino-[2,1-b][3,8]-phenanthrolin-2(1H)-yl)-benzene sulfonic acid and 5-methyl-2-(1,3,6-triketo-3,6-dihydrobenzimid-azo[2,1-b]benzo[lmn][3,8]-phenanthroline-2(1H)-yl)benzene sulfonic acid.

* * * * *